US006627175B2

(12) United States Patent
Schoebrechts

(10) Patent No.: US 6,627,175 B2
(45) Date of Patent: Sep. 30, 2003

(54) PROCESS FOR THE MANUFACTURE OF A CRYSTALLINE SOLID

(75) Inventor: Jean-Paul Schoebrechts, Grez-Doiceau (BE)

(73) Assignee: Solvay (Societe Anonyme), Brussels (BE)

( * ) Notice: Subject to any disclaimer, the term of this patent is extended or adjusted under 35 U.S.C. 154(b) by 311 days.

(21) Appl. No.: 09/785,286

(22) Filed: Feb. 20, 2001

(65) Prior Publication Data

US 2001/0041162 A1 Nov. 15, 2001

(30) Foreign Application Priority Data

Feb. 17, 2000 (EP) .............................................. 00200533

(51) Int. Cl.$^7$ .................. C01B 37/00; C01B 39/06; C07D 301/12
(52) U.S. Cl. .................. 423/713; 423/326; 423/707; 549/531
(58) Field of Search ................ 423/713, 326, 423/305, 306, 707; 549/523, 531

(56) References Cited

U.S. PATENT DOCUMENTS

| | | | |
|---|---|---|---|
| 4,410,501 A | | 10/1983 | Taramasso et al. |
| 4,666,692 A | | 5/1987 | Taramasso et al. |
| 5,124,136 A | * | 6/1992 | Davis .......................... 423/705 |
| 5,160,500 A | * | 11/1992 | Chu et al. ................... 585/486 |
| 5,885,546 A | * | 3/1999 | Kumar et al. ............... 423/703 |
| 6,054,112 A | * | 4/2000 | Hasenzahl et al. .......... 423/705 |

FOREIGN PATENT DOCUMENTS

| | | |
|---|---|---|
| DE | 196 23 972 | 12/1997 |
| WO | WO 99/28029 | 6/1999 |

OTHER PUBLICATIONS

A. Thangaraj, et al., Zeolites, vol. 12, pp. 943–950, "Studies on the Synthesis of Titanium Silicalite, TS–1," Nov./Dec. 1992.
K.T. Jung, et al., Microporous and Mesoporous Materials, vol. 21, pp. 281–288, "A New Method for the Synthesis of TS–1 Monolithic Zeolite," 1998.
G. Zhang, et al., Chem. Mater., vol. 9, pp. 210–217, "Preparation of Colloidal Suspensions of Discrete TS–1 Crystals," 1997.
A. Tuel, Catalysis Letters, vol. 51, pp. 59–63, "Crystallization of TS–1 in the Presence of Alcohols: Influence on Ti Incorporation and Catalytic Activity," 1998.
B. Notari, Heterogenous Catalysis, pp. 243–256, "Titanium Silicalite: A New Selective Oxidation Catalyst," 1991.

* cited by examiner

*Primary Examiner*—David Sample
(74) *Attorney, Agent, or Firm*—Oblon, Spivak, McClelland, Maier & Neustadt, P.C.

(57) ABSTRACT

Process for the manufacture of crystalline solids comprising at least one element chosen from Groups IIIa, IVa and Va and at least one transition metal, according to which at least one source of oxide of the element from Groups IIIa, IVa and Va and at least one transition metal oxide source, which was dissolved beforehand in an alcohol having a $pK_a$ below that of water, are hydrolysed in an aqueous medium comprising a mineralizing agent and the gel thus obtained is crystallized in the presence of a structuring agent.

18 Claims, No Drawings

PROCESS FOR THE MANUFACTURE OF A CRYSTALLINE SOLID

The present invention relates to the manufacture of crystalline solids and in particular of titanium zeolites.

The first syntheses of titanium zeolites described in the literature form the subject-matter of U.S. Pat. Nos. 4,666,692 and 4,410,501, the latter being specific to titanium silicalites. The method of synthesis used consists of a hydrothermal treatment of a gel obtained by reaction between a hydrolysable silicon oxide source (such as an alkoxide), a titanium alkoxide, optionally an alkaline oxide, tetrapropyl-ammonium hydroxide, which acts both as mineralizing agent (which gives the OH$^-$ ions necessary for the hydrolysis) and as structuring agent (which influences the crystalline structure), and water. When it is desired to incorporate large amounts of titanium in the silicalite, the source of titanium oxide, more reactive than that of the silicon oxide, must be treated beforehand with an $H_2O_2$ solution in order to avoid the precipitation of titanium oxide in anatase form outside the crystal lattice. This treatment and the subsequent addition of the nitrogenous organic base are carried out slowly and under cold conditions, which renders the manufacturing process laborious. In addition, before crystallization of silicalite, the alcohols resulting from the hydrolysis of the silicon and titanium alkoxides are evaporated. This evaporation takes time, consumes energy and furthermore constitutes a difficult operation to carry out on industrial scale, which additionally requires adjustment of the water content after evaporation.

Thangaraj et al. (Zeolites, 1992, Vol. 12, November/December, p. 943–950) have proposed a modified procedure for the synthesis of TS-1 which makes it possible to overcome the use of $H_2O_2$ solutions and to incorporate larger amounts of titanium in the lattice. This method consists in adding a first portion of the solution of the nitrogenous organic base (TPAOH or tetra-n-propylammonium hydroxide) to STEO (silicon tetraethoxide) and in adding TTBO (titanium tetra-n-butoxide), in solution in iPrOH (isopropyl alcohol), dropwise to the combined mixture. After stirring, the remainder of the solution of the nitrogenous organic base is added and the mixture is heated to evaporate the alcohol. This method exhibits the disadvantage of using an alcoholic solution of TTBO, which is not very stable with respect to hydrolysis, and thus promotes the formation of titanium oxide precipitates. In addition, it includes a stage of evaporation of the alcohols present in the gel before crystallization.

Recently, Tuel (Catalysis Letters, 51, 1998, p. 59–63) has shown that TS-1 can be synthesized starting with the same reactants without evaporation of the isopropyl (iPrOH), ethyl (EtOH) and n-butyl (nBuOH) alcohols present in the gel, without this having an effect on the crystalline structure and the catalytic activity of the TS-1 when it is used as catalyst for reactions for the hydroxylation of phenols with $H_2O_2$. Nevertheless, this method still exhibits the disadvantage of using an alcoholic solution of the titanium alkoxide, which is not very stable with respect to hydrolysis, which solution thus has to be used rapidly and carefully after its manufacture.

The Applicant Company has found that, surprisingly, during the synthesis of crystalline solids starting from at least one source of oxide of the element from Groups IIIa, IVa and Va and from at least one transition metal oxide source, the choice of an alcohol having a $pK_a$ below that of water to dissolve the transition metal oxide source makes it possible to obtain a stable solution which does not result in the formation of precipitate during addition of this solution to the aqueous hydrolysis medium and which can be stored before it is used. In addition, this alcohol can remain present during the crystallization without affecting the crystalline structure and the catalytic activity of the crystalline solid obtained.

Consequently, the fact of using alcohol having a $pK_a$ below that of water to dissolve the source of the oxide of the transition metal makes it possible to obtain crystalline solids according to a process which is easy to employ and which makes it possible to easily reduce, indeed even to avoid, the formation of metal oxide precipitates outside the crystal lattice, such as, for example, anatase.

The present invention consequently relates to a process for the manufacture of crystalline solids comprising at least one element chosen from Groups IIIa, IVa and Va and at least one transition metal, according to which at least one source of oxide of the element from Groups IIIa, IVa and Va and at least one transition metal oxide source, which was dissolved beforehand in an alcohol having a $pK_a$ below that of water, are hydrolysed in an aqueous medium comprising a mineralizing agent and the gel thus obtained is crystallized in the presence of a structuring agent.

The crystalline solids according to the present invention denote all the solids where the atoms are arranged so as to define a crystal lattice and which comprise at least one element chosen from Groups IIIa, IVa and Va and at least one transition metal. The element from Groups IIIa, IVa and Va can be aluminium, silicon or phosphorus. This element is preferably silicon. The transition metal can be titanium, vanadium, zirconium, chromium, iron or cobalt. This metal is preferably titanium.

These crystalline solids are advantageously zeolites. They are preferably titanium zeolites. The term "titanium zeolite" is understood to denote a solid comprising silica which exhibits a microporous crystalline structure of zeolite type and in which several silicon atoms are replaced by titanium atoms. The titanium zeolite advantageously exhibits a crystalline structure of ZSM-5 or ZSM-11 type. It can also exhibit a crystalline structure of zeolite β type devoid of aluminium. It preferably exhibits an infrared absorption band at approximately 950–960 cm$^{-1}$. Titanium zeolites of silicalite type are highly suitable. Those corresponding to the formula $xTiO_2(1-x)SiO_2$, in which x is from 0.0001 to 0.5, preferably from 0.001 to 0.05, have an excellent performance. Materials of this type, known under the name of TS-1, exhibit a microporous crystalline zeolite structure analogous to that of zeolite ZSM-5. The properties and the main applications of these compounds are known (B. Notari; Structure-Activity and Selectivity Relationship in Heterogeneous Catalysis; R. K. Grasselli and A. W. Sleight Editors; Elsevier; 1991; p. 243–256).

The source of oxide of the element resulting from Groups IIIa, IVa and Va is a hydrolysable compound of this element, such as, for example, the alkoxides of this element. When it is silicon, the source can be chosen from colloidal silica, alkali metal or alkaline earth metal silicates, and silicon alkoxides. The latter are particularly well suited.

The transition metal oxide source according to the invention can be a transition metal halide, such as, for example, $TiCl_3$, or a transition metal alkoxide. Transition metal alkoxides are particularly well suited. Titanium alkoxides give good results.

The term "silicon or titanium alkoxides" is understood to denote compounds corresponding to the general formula $M(OR)_4$ where M is either silicon or titanium and R is a hydrocarbonaceous group. The silicon alkoxide is preferably a silicon tetraalkoxide. The alkoxide group advantageously comprises up to 10 carbon atoms, preferably up to 6 carbon atoms and more particularly up to 4 carbon atoms. Silicon tetraethoxide or STEO gives good results. The titanium alkoxide is preferably a titanium tetraalkoxide. The alkoxide group advantageously comprises up to 10 carbon atoms, preferably up to 6 carbon atoms and more particularly up to 4 carbon atoms. With the process according to the invention, good results are obtained when the titanium alkoxide is derived from an alcohol which has a $pK_a$ above that of water. Examples of such alcohols are ethanol, propanol and butanol. Titanium tetra-n-butoxide or TTBO gives excellent results.

The mineralizing agent, which supplies the hydroxide ions necessary for hydrolysis of the sources of oxide of the element from Groups IIIa, IVa and Va and of the transition metal oxide, and the structuring agent, which promotes the crystallization towards the appropriate crystalline structure, can be two separate compounds, such as, respectively, alkali metal or alkaline earth metal bases, on the one hand, and amines, phosphines, ammonium salts, phosphonium salts, alcohols or amino acids, on the other hand. Alternatively, they can be one and the same compound, such as a quaternary ammonium base. Tetraalkylammonium bases (the alkyl being able to comprise up to 10 carbon atoms, in particular up to 6 carbon atoms, preferably up to 4 carbon atoms), such as tetra-n-propylammonium hydroxide or TPAOH, are particularly well suited to acting both as mineralizing agent and as structuring agent. Tetraethylammonium hydroxide or tetra-n-butylammonium hydroxide are also well suited. However, it can prove to be economically advantageous to replace a portion of this base with the corresponding tertiary amine. Thus, the base can be mixed with the amine in amounts such that the (amine)/(base+amine) molar ratio is from 1 to 35%, in particular from 20 to 30%, for example approximately 25%. Good results are obtained in particular by mixing TPAOH with tripropylamine in these proportions.

The mineralizing agent is generally an aqueous solution at a concentration by weight of greater than or equal to 10% and preferably of greater than or equal to 15%. The concentration by weight of mineralizing agent is preferably of less than or equal to 50%, indeed even of less than or equal to 25%. A concentration of approximately 20% gives good results.

The solution of mineralizing agent is generally depleted in alkali metals and alkaline earth metals. It preferably comprises less than 200 ppm, indeed even less than 25 ppm, of these metals and ideally less than 2 ppm.

In the context of the invention, it is advisable for the term "alcohol" to be accepted in the entirely general sense and to include phenols (unsubstituted and partially or completely substituted phenols) just as easily as linear or cyclic, saturated or unsaturated, and unsubstituted and partially or completely substituted aliphatic alcohols. Aliphatic alcohols are particularly recommended. Those which comprise up to 10 carbon atoms are well suited, in particular up to 6 carbon atoms, for example up to 4 carbon atoms. Examples of aliphatic alcohols having a $pK_a$ below that of water in accordance with the invention are 2,2,2-trifluoroethanol, 2-methoxyethanol and 2-ethoxyethanol (EtOEtOH). The latter gives good results.

Likewise, in the context of this invention, it is advisable for the term "gel" to be accepted in the broad sense which ranges from the simple solution (fluid) to a true gel with a high consistency.

It may be advantageous to heat the solution obtained by dissolution of the transition metal oxide source in the alcohol having a $pK_a$ below that of water. To this end, this solution is generally heated to a temperature of at least 30° C., in particular of at least 32° C. The temperature usually does not exceed 50° C., in particular does not exceed 40° C., a temperature in the region of 35° C. giving good results. The period during which the solution can be heated is commonly at least 1 min, in particular at least 10 min. The period generally does not exceed 60 min, in particular does not exceed 45 min. A period in the region of 30 min gives good results.

The reactants participating in the formation of the gel to be crystallized, that is to say the source of oxide of the element resulting from Groups IIIa, IVa and Va, the transition metal oxide source in the alcoholic solution, the water and the mineralizing agent can be mixed in any order, care being taken, however, not to form a transition metal oxide precipitate.

One possible method consists in first mixing the source of oxide of the element resulting from Groups IIIa, IVa and Va, the transition metal oxide source and the alcohol and in subsequently slowly adding an aqueous solution of the mineralizing agent, preferably under cold conditions (from 0 to 5° C.).

According to another method, a first solution is prepared by mixing the source of oxide of the element resulting from Groups IIIa, IVa and Va with a first fraction of an aqueous solution of the mineralizing agent; a second solution is prepared by mixing the transition metal oxide source with the alcohol; these two solutions are mixed and a second fraction of the solution of the mineralizing agent is added to this mixture. In this method, the fraction of the solution of the mineralizing agent added to the source of oxide of the element resulting from Groups IIIa, IVa and Va is generally greater than 60% of the total fraction of mineralizing agent, preferably greater than 70%. It advantageously does not exceed 99%, indeed even 90%. This second method has two advantages with respect to the first: firstly, it makes it possible to reduce the proportion of transition metal which is not introduced into the crystal lattice and, secondly, it makes it possible to carry out the hydrolysis operation at ambient temperature and not under cold conditions and in a shorter time.

According to yet another method, a first solution is first prepared by mixing the source of oxide of the element resulting from Groups IIIa, IVa and Va with all the mineralizing agent, a second solution is subsequently prepared by mixing the transition metal oxide source with the alcohol and the two solutions are mixed.

The durations, that is to say the speeds, of these mixing and stirring operations are adjusted so as to avoid the formation of a precipitate.

The abovementioned mixing operations are preferably carried out under nitrogen. They can be followed by an evaporation of the alcohols by heating at a temperature of at least 60° C., indeed even of at least 75° C. This temperature is generally of less than or equal to 100° C., preferably of less than or equal to 90° C. A temperature in the region of 85° C. is highly suitable. The duration of heating is preferably that needed for complete removal of the alcohols. It can vary between 1 h and 10 h, in particular between 3 and 5 h.

The gels, devoid or not devoid of alcohols, can subsequently have water and/or alcohol added in order to adjust their compositions before crystallization.

The fact of carrying out the crystallization in the presence of alcohol(s) surprisingly makes it possible to increase the yield of solids from the reaction (that is to say, the mass of solid recovered after calcination with respect to its theoretical value calculated on the basis of the masses of precursors of oxide of the element resulting from Groups IIIa, IVa and Va and of transition metal employed).

The composition of the gel before crystallization generally exhibits:
- a molar ratio (transition metal/element resulting from Groups IIIa, IVa and Va) generally of greater than or equal to 0.0005 mol/mol and preferably of greater than or equal to 0.001 mol/mol; this molar ratio generally does not exceed 0.1 mol/mol and preferably does not exceed 0.05 mol/mol;
- a molar ratio (mineralizing and structuring agent/element resulting from Groups IIIa, IVa and Va) generally of greater than or equal to 0.05 mol/mol and preferably of greater than or equal to 0.1 mol/mol; this molar ratio generally does not exceed 1 mol/mol and preferably does not exceed 0.5 mol/mol; values of 0.12 to 0.3 being standard;
- a molar ratio ($H_2O$/element resulting from Groups IIIa, IVa and Va) generally of greater than or equal to 5 mol/mol and preferably of greater than or equal to 10 mol/mol; this molar ratio generally does not exceed 200 mol/mol and preferably does not exceed 100 mol/mol; values from 10 to 40 being standard;
- a molar ratio (alcohol resulting from the hydrolysis of the source of oxide of the element resulting from Groups IIIa, IVa and Va/element resulting from Groups IIIa, IVa and Va) generally of greater than or equal to 0 mol/mol; this molar ratio generally does not exceed 4 mol/mol;
- a molar ratio (alcohol resulting from the hydrolysis of the transition metal oxide source/element resulting from Groups IIIa, IVa and Va) generally of greater than or equal to 0 mol/mol; this molar ratio generally does not exceed 0.2 mol/mol;
- a molar ratio (alcohol which dissolves the transition metal oxide source/element resulting from Groups IIIa, IVa and Va) generally of greater than or equal to 0.002 mol/mol and preferably of greater than or equal to 0.1 mol/mol; this molar ratio generally does not exceed 10 mol/mol and preferably does not exceed 8 mol/mol; values from 0.75 to 5 being standard.

The gel to be crystallized is generally at an alkaline pH and preferably at a pH at least equal to 10.

The crystallization is generally carried out during a heat treatment which can take place in an autoclave.

The term "autoclave" is used to describe a hermetically sealed container enjoying the appropriate mechanical strength and chemical resistance to be able to withstand the pressure, the temperature and the reactants present within it. This container is additionally provided with one or more thermal conditioning and stirring means. It is also provided with temperature and pressure regulation means and with appropriate safety devices.

The duration of the heat treatment is preferably greater than or equal to 1 h, indeed even greater than or equal to 5 h. The duration of the heat treatment preferably does not exceed 120 h, indeed even 72 h, durations of 10 to 24 h being standard.

The mean temperature during the heat treatment is generally greater than or equal to 100° C., preferably greater than or equal to 130° C. It is generally less than or equal to 220° C., preferably less than or equal to 200° C., temperatures of 150 to 180° C. being standard, for example approximately 175° C.

After crystallization, the solid particles in suspension can be separated from the liquid reaction medium by conventional means (centrifuging, filtration, spraying, and the like) and can be optionally washed.

The crystallized particles, separated or not separated from the liquid reaction medium, are preferably dried. Drying can be carried out in any known way.

The crystallized particles, dried or undried, are generally subjected to calcination, preferably under air. The duration of calcination is generally greater than or equal to 1 h, preferably greater than or equal to 2 h. The duration of calcination is generally less than or equal to 72 h, preferably less than or equal to 24 h, durations of 5 to 15 h being standard. The calcination temperature is generally greater than or equal to 400° C., preferably greater than or equal to 500° C. The calcination temperature is generally less than or equal to 650° C., generally less than or equal to 600° C. It is, for example, approximately 550° C.

The process according to the invention can advantageously be integrated in a process for the manufacture of an oxirane by reaction between an olefinic compound, preferably allyl chloride or propylene, and a peroxide compound, preferably hydrogen peroxide.

The process according to the invention consequently also relates to a process for the manufacture of an oxirane in which a crystalline solid is manufactured according to the method described above and this crystalline solid is used as catalyst for the reaction between an olefinic compound, preferably allyl chloride or propylene, and peroxide compound, preferably hydrogen peroxide.

The present invention is illustrated without implied limitation by the following examples. The experimental conditions relating to these examples are described below and the results appear in Table 1.

EXAMPLE C1

Not in Accordance with the Invention 35 g of STEO (approximately 38 ml) and 0.96 g (0.89 ml) of TTEO were mixed with air excluded and the mixture was stirred at 35° C. under nitrogen for 30 min.

The mixture was subsequently cooled to 0° C. under nitrogen and with stirring, in order to add thereto 47.5 g (47.5 ml) of a 20% by weight aqueous TPAOH solution according to the following rate of addition profile: 0.1 ml/min for the first 2 ml, 0.2 ml/min for the following 2, 0.5 ml/min for the following 4 and 1.0 ml/min for the balance.

The appearance of a precipitate was observed during the addition of the first 2 ml, of flocculation between 2 and 4 ml and of redissolution between 4 and 47.5 ml.

The solution obtained was brought to 65° C. over 0.5 h and remained there under nitrogen and with stirring for 3 h.

An amount of water equal to approximately 67 ml was added.

The combined mixture was heated in an autoclave at 175° C. for 64 h and then filtered under a pressure of 7 bar through a 0.025 μm Millipore filter.

The solid collected was dried in an oven at 90° C. overnight and then calcined under air for 10 h at 550° C. The yield of solid from the reaction was then calculated.

A fraction of the silicalite obtained was analyzed by ICP-OAS for the purpose of determining its titanium content and by XRD (X-ray diffraction) for the purpose of determining its anatase content.

Another fraction of the silicalite obtained was used in a test of epoxidation of ALC (allyl chloride) with dilute $H_2O_2$ (30–35% by weight) under the following conditions:

solvent=$CH_3OH$, 25° C., 750 rpm, 2.6 mol ALC/kg, 1.3 mol $H_2O_2$/kg, ALC/$H_2O_2$=2 mol/mol, $CH_3OH$/ALC=7.2 mol/mol, 2% by weight of catalyst comprising 20 g Ti/kg. The $H_2O_2$ is added over 20 min, so as to limit the increase in the temperature of the reaction medium. Samples are withdrawn after reacting for 21 and 90 min. They are analysed by iodometry, for the determination of the residual $H_2O_2$ content, and by gas chromatography, for the determination of the organic compounds (only the fraction collected at the end of the reaction, i.e. at 90 min).

EXAMPLE 2

In Accordance with the Invention

The procedure followed is identical to that described above for Example 1, except as regards the following points:

EtOEtOH (0.1 mol/mol with respect to Si) was added to the mixture of STEO and TTEO evaporation of the alcohols was carried out at 85° C.

the recovery of the solid after heat treatment was carried out by ultracentrifugation.

The formation of a precipitate was not observed during the addition of the TPAOH to the mixture of STEO, TTEO and EtOEtOH.

EXAMPLE C3

Not in Accordance with the Invention

The procedure which was followed is in accordance with that recommended by Thangaraj and comprises the following stages:

dissolution under nitrogen of TTBO (1.86 g) in dry isopropanol (iPrOH) (13.3 ml) and stirring at 35° C. for 30 min addition to STEO (47.7 g) of a portion of the 20% by weight aqueous TPAOH solution (48.2 ml added over 10 min at 25° C.) and stirring for 15 min addition under nitrogen and at ambient temperature of the TTBO solution to the prehydrolysed STEO (16 ml/h) and holding at this temperature for 30 min addition of the remaining TPAOH (16 ml at 16 ml/h) to the preceding mixture the continuation of the operations is identical to that in Example 2 (evaporation of the alcohols, heat treatment, calcination and analyses).

A slight precipitate is observed at the end of the tube for injection of the solution of TTBO in iPrOH.

EXAMPLE 4

In Accordance with the Invention

The procedure followed is identical to that described above for Example 3, except that 2-ethoxyethanol (EtOEtOH) was used instead of iPrOH and that the duration of crystallization was 136 h.

Precipitate was not observed at the end of the tube for injection of the solution of TTBO in EtOEtOH.

EXAMPLE 5

In Accordance with the Invention

The procedure followed is identical to that described above for Example 3, except as regards the following points:

the amounts of reactants used lead to a gel with the molar composition 1 Si—0.034 Ti—0.28 TPAOH—28 $H_2O$—4.9 alcohol;

the nature of the alcohol: EtOEtOH;

the fact that the alcohols were not evaporated before the crystallization;

the duration of the crystallization: 18 h;

the fact that the recovery of the solids was carried out by spraying.

The solutions of TTBO in this alcohol are stable to the air for several days and are thus easier to handle than the solutions of TTBO in iPrOH.

TABLE 1

| | | | | | | | | |
|---|---|---|---|---|---|---|---|---|
| | | | | | Experimental conditions and results | | | |
| Example (No.) | Duration of crystallization (h) | Yield of solid (weight %) | [Titanium] (g/kg) | Molar fraction of Ti in anatase form | $H_2O_2$ conversion after 21 min (mol %) | $H_2O_2$ conversion after 90 min (mol %) | EPI/$H_2O_2$ selectivity after 90 min (mol %) | EPI/C3 selectivity after 90 min (mol %) |
| C1 | 64 | 80 | 19 | 0.33 | 40 | 99 | 97 | 98 |
| 2 | 64 | 86 | 20 | 0.25 | 39 | 96 | 95 | 97 |
| C3 | 66 | 86 | 20 | 0.26 | 40 | 99 | 97 | 97 |
| 4 | 136 | 99 | 18 | 0.11 | 43 | 100 | 93 | 97 |
| 5 | 18 | 98 | 18 | <0.02 | 64 | 100 | 99 | 99 |

This application is based on EP 00200533.8, filed Feb. 17, 2000, the entire contents of which are hereby incorporated by reference.

What is claimed is:

1. A process, comprising:

dissolving, in an alcohol having a $pK_a$ below that of water:

at least one titanium oxide source, to obtain a solution;

contacting said solution with:

at least one silicon oxide source and optionally at least one selected from the group consisting of Group IIIa oxide source, Group Va oxide source, and mixtures thereof, and an aqueous medium comprising a mineralizing agent;

and hydrolyzing to obtain a gel; and crystallizing said gel in the presence of at least one structuring agent;

to obtain a titanium zeolite comprising at least one titanium oxide and at least one silicon oxide and optionally at least one selected from the group consisting of Group IIIa oxide, Group Va oxide and mixtures thereof.

2. A process according to claim 1, wherein said titanium zeolite is a TS-1 titanium zeolite.

3. A process according to claim 1, wherein the silicon oxide source comprises silicon alkoxide.

4. A process according to claim 1, wherein the silicon oxide source comprises silicon tetraethoxide.

5. A process according to claim 1, wherein the titanium oxide source comprises titanium alkoxide.

6. A process according to claim 1, wherein the titanium oxide source comprises titanium tetra-n-butoxide.

7. A process according to claim 1, wherein the alcohol is 2-ethoxyethanol.

8. A process according to claim 1, wherein said mineralizing agent and said structuring agent are the same compound.

9. A process according to claim 1, wherein said mineralizing agent and said structuring agent comprise tetraalkylammonium hydroxide.

10. A process according to claim 1, wherein said mineralizing agent and said structuring agent comprise tetra-n-propylammonium hydroxide.

11. A process according to claim 1, wherein said aqueous medium comprises tetraalkylammonium hydroxide and a corresponding tertiary amine.

12. A process according to claim 1, comprising:
preparing a first solution by mixing:
the silicon oxide source, and
optionally, the Group IIIa oxide source, Group Va oxide source, or Group IIIa and Group Va oxide sources, with a first fraction of the aqueous solution of the mineralizing agent;
preparing a second solution by mixing the titanium oxide source with the alcohol; and
mixing said first and second solutions with a second fraction of the aqueous solution of the mineralizing agent.

13. A process according to claim 1, wherein, prior to the crystallizing, said gel is not subjected to evaporation of the alcohol.

14. A process according to claim 13, wherein, prior to the crystallizing, said gel comprises the alcohol.

15. A process according to claim 1, wherein said titanium zeolite comprises a catalyst.

16. A process according to claim 1, further comprising catalyzing, with said titanium zeolite, a reaction between:
an olefinic compound, and
a peroxide compound,
to obtain an oxirane.

17. A process according to claim 16, wherein said olefinic compound is allyl chloride or propylene.

18. A process according to claim 16, wherein said peroxide compound is hydrogen peroxide.

* * * * *